(12) United States Patent
Abbott et al.

(10) Patent No.: US 11,071,801 B2
(45) Date of Patent: Jul. 27, 2021

(54) RELEASE OF CLO$_2$ GAS FROM MEDICAL DEVICE PACKAGING FILM

(71) Applicants: Wisconsin Alumni Research Foundation, Madison, WI (US); Bemis Company, Inc., Neenah, WI (US)

(72) Inventors: Nicholas Abbott, Madison, WI (US); Rishabh Jain, Appleton, WI (US); Kevin Nelson, Neenah, WI (US); David Busche, Neenah, WI (US); David Lynn, Middleton, WI (US)

(73) Assignees: Wisconsin Alumni Research Foundation, Madison, WI (US); Bemis Company, Inc., Neenah, WI (US)

( * ) Notice: Subject to any disclaimer, the term of this patent is extended or adjusted under 35 U.S.C. 154(b) by 0 days.

(21) Appl. No.: 15/433,510

(22) Filed: Feb. 15, 2017

(65) Prior Publication Data

US 2017/0157904 A1    Jun. 8, 2017

Related U.S. Application Data

(63) Continuation of application No. PCT/US2015/047608, filed on Aug. 18, 2016.
(Continued)

(51) Int. Cl.
*C01B 11/02* (2006.01)
*A61L 2/20* (2006.01)
(Continued)

(52) U.S. Cl.
CPC .............. *A61L 2/20* (2013.01); *A23B 7/144* (2013.01); *B01J 19/123* (2013.01); *B32B 1/02* (2013.01);
(Continued)

(58) Field of Classification Search
CPC ....... A01N 59/00; A23L 3/3409; A23L 3/358; B32B 7/02; B32B 15/082; B32B 15/085;
(Continued)

(56) References Cited

U.S. PATENT DOCUMENTS 3,754,079 A    8/1973    Callerame
4,456,511 A    6/1984    Fisher
(Continued)

FOREIGN PATENT DOCUMENTS

CN    102834350 A    12/1919
CN    1355768 A    6/2002
(Continued)

OTHER PUBLICATIONS

U.S. Appl. No. 62/206,464, filed Aug. 18, 2015, Wisconsin Alumni Research Foundation.
(Continued)

*Primary Examiner* — Ellen S Hock
(74) *Attorney, Agent, or Firm* — Mueting Raasch Group

(57) ABSTRACT

A multilayer medical packaging film includes a first layer and a chlorine dioxide-producing layer. The chlorine dioxide-producing layer includes a polymer composition and a plurality of chlorite ions. The chlorine dioxide-producing layer is substantially free of an energy-activated catalyst and is substantially free of an acid-releasing compound. However, the film is capable of generating chlorine dioxide when exposed to UV light and moisture.

19 Claims, 2 Drawing Sheets

Related U.S. Application Data

(60) Provisional application No. 62/206,464, filed on Aug. 18, 2015.

(51) Int. Cl.

| | | |
|---|---|---|
| *B32B 27/18* | (2006.01) | |
| *B32B 27/30* | (2006.01) | |
| *B32B 27/32* | (2006.01) | |
| *B32B 7/12* | (2006.01) | |
| *B32B 27/36* | (2006.01) | |
| *B32B 27/28* | (2006.01) | |
| *B32B 7/02* | (2019.01) | |
| *B32B 27/34* | (2006.01) | |
| *B32B 15/08* | (2006.01) | |
| *B65D 1/00* | (2006.01) | |
| *B32B 1/02* | (2006.01) | |
| *B32B 15/082* | (2006.01) | |
| *B32B 15/085* | (2006.01) | |
| *B32B 15/20* | (2006.01) | |
| *B32B 27/08* | (2006.01) | |
| *B32B 27/20* | (2006.01) | |
| *B65D 65/40* | (2006.01) | |
| *B65D 81/24* | (2006.01) | |
| *A23B 7/144* | (2006.01) | |
| *C08L 23/12* | (2006.01) | |
| *B01J 19/12* | (2006.01) | |
| *C08K 3/24* | (2006.01) | |

(52) U.S. Cl.
CPC .................. *B32B 7/02* (2013.01); *B32B 7/12* (2013.01); *B32B 15/08* (2013.01); *B32B 15/082* (2013.01); *B32B 15/085* (2013.01); *B32B 15/20* (2013.01); *B32B 27/08* (2013.01); *B32B 27/18* (2013.01); *B32B 27/20* (2013.01); *B32B 27/28* (2013.01); *B32B 27/30* (2013.01); *B32B 27/304* (2013.01); *B32B 27/306* (2013.01); *B32B 27/32* (2013.01); *B32B 27/322* (2013.01); *B32B 27/34* (2013.01); *B32B 27/36* (2013.01); *B65D 1/00* (2013.01); *B65D 65/40* (2013.01); *B65D 81/24* (2013.01); *C01B 11/024* (2013.01); *C08K 3/24* (2013.01); *C08L 23/12* (2013.01); *A61L 2202/11* (2013.01); *B01J 2219/0879* (2013.01); *B01J 2219/1203* (2013.01); *B32B 2255/10* (2013.01); *B32B 2255/20* (2013.01); *B32B 2255/205* (2013.01); *B32B 2264/10* (2013.01); *B32B 2307/40* (2013.01); *B32B 2307/50* (2013.01); *B32B 2307/71* (2013.01); *B32B 2307/7242* (2013.01); *B32B 2307/7244* (2013.01); *B32B 2307/7246* (2013.01); *B32B 2307/732* (2013.01); *B32B 2307/748* (2013.01); *B32B 2315/00* (2013.01); *B32B 2323/10* (2013.01); *B32B 2405/00* (2013.01); *B32B 2439/06* (2013.01); *B32B 2439/46* (2013.01); *B32B 2439/70* (2013.01); *B32B 2439/80* (2013.01); *C08L 2203/16* (2013.01)

(58) Field of Classification Search
CPC ....... B32B 15/20; B32B 27/28; B32B 27/306; B32B 27/32; B32B 2439/80; B32B 2307/7244; B65D 81/24; B65D 65/40; A61L 2/20; A61L 2202/11
USPC .......... 428/34.1, 35.7; 424/405, 408
See application file for complete search history.

(56) References Cited

U.S. PATENT DOCUMENTS

| | | |
|---|---|---|
| 4,585,482 A | 4/1986 | Tice et al. |
| 4,874,489 A | 10/1989 | Callerame |
| 5,360,528 A | 11/1994 | Oh et al. |
| 5,360,609 A | 11/1994 | Wellinghoff |
| 5,631,300 A | 5/1997 | Wellinghoff |
| 5,695,814 A | 12/1997 | Wellinghoff et al. |
| 5,719,100 A | 2/1998 | Zahradnik |
| 5,888,528 A | 3/1999 | Wellinghoff et al. |
| 5,922,776 A * | 7/1999 | Wellinghoff ............ A01N 59/00 514/772.3 |
| 5,965,264 A | 10/1999 | Barenberg et al. |
| 5,980,826 A | 11/1999 | Barenberg et al. |
| 6,231,830 B1 | 5/2001 | Madray |
| 6,554,887 B1 * | 4/2003 | Inglis ...................... A01M 1/14 206/484.1 |
| 6,605,304 B1 | 8/2003 | Wellinghoff et al. |
| 6,767,509 B1 | 7/2004 | Griesbach et al. |
| 7,273,567 B1 | 9/2007 | Wellinghoff et al. |
| 7,449,194 B2 | 11/2008 | Lelah et al. |
| 7,695,692 B2 | 4/2010 | Sanderson |
| 8,652,411 B2 | 2/2014 | Taguchi et al. |
| 2005/0079124 A1 | 4/2005 | Sanderson |
| 2005/0106380 A1 | 5/2005 | Gray et al. |
| 2006/0006361 A1 | 1/2006 | Callerame |
| 2006/0068029 A1 | 3/2006 | Mason |
| 2006/0178445 A1 | 8/2006 | McIntyre |
| 2008/0026029 A1 | 1/2008 | Wellinghoff et al. |
| 2008/0299066 A1 | 12/2008 | Wellinghoff et al. |
| 2009/0008238 A1 | 1/2009 | Williams |
| 2009/0220739 A1 | 9/2009 | Chougule |
| 2012/0164025 A1 | 6/2012 | Stockley, III et al. |
| 2014/0311094 A1 | 10/2014 | Thompson et al. |
| 2014/0348702 A1 | 11/2014 | Wofford et al. |
| 2015/0024211 A1 | 1/2015 | Miratsu et al. |
| 2018/0243456 A1 | 8/2018 | Abbott et al. |

FOREIGN PATENT DOCUMENTS

| | | |
|---|---|---|
| CN | 101195477 A | 6/2008 |
| EP | 611162 * | 2/1994 |
| EP | 1198412 B1 | 12/2008 |
| WO | WO 00/69775 A1 | 11/2000 |
| WO | WO 2010/045280 A2 | 4/2010 |
| WO | WO 2016/069864 A2 | 5/2016 |
| WO | PCT/US2016/047603 | 8/2016 |
| WO | PCT/US2016/047612 | 8/2016 |
| WO | WO 2017/031345 A1 | 2/2017 |
| WO | WO 2017/031351 A1 | 2/2017 |
| ZA | 2001/9124 B | 11/2001 |

OTHER PUBLICATIONS

Aieta et al. "Determination of chlorine dioxide, chlorine, chlorite, and chlorate in water" 1984 *American Water Works Association* pp. 64-70.

Appendini et al. "Review of antimicrobial food packaging" 2002 *Innovative Food Science & Emerging Technologies* vol. (3):pp. 113-126.

Burton et al. "Effect of gaseous chlorine dioxide on indoor microbial contaminants" 2008 *Journal of the Air & Waste Management Association* vol. (58):pp. 647-656.

Buxton et al. Radiation chemistry and photochemistry of oxychlorine ions. Part 1, 2 and 3—1972 *Journal of the Chemical Society, Faraday Transactions 1: Physical Chemistry in Condensed Phases* vol. (68):pp. 947-977.

Cosson et al., "Photodecomposition of Chlorine Dioxide and Sodium Chlorite in Aqueous Solution by Irradiation with Ultraviolet Light" 1994 *Industrial and Engineering Chemistry Research*, vol. (33):pp. 1468-1475.

Diffey "Sources and measurement of ultraviolet radiation" 2002 *Methods* vol. (28):pp. 4-13.

(56) References Cited

OTHER PUBLICATIONS

Gagnon et al. "Disinfectant efficacy of chlorite and chlorine dioxide in drinking water biofilms" 2005 *Water Research* vol. (39):pp. 1809-1817.

Gibbs et al. "Gaseous chlorine dioxide as an alternative for bedbug control" 2012 *Infection Control and Hospital Epidemiology* vol. (33):pp. 495-499.

Gómez-López et al. "Chlorine dioxide for minimally processed produce preservation: a review" 2009 *Trends in Food Science & Technology* vol. (20):pp. 17-26.

Gordon et al. "The chemistry of chlorine dioxide" 1972 *Progress in Inorganic Chemistry* vol. (15):pp. 201-286.

Han "Antimicrobial food packaging" 2003 *Novel food packaging techniques* pp. 50-70.

Hirneisen et al. "Viral Inactivation in Foods: A Review of Traditional and Novel Food-Processing Technologies" 2010 *Comprehensive Reviews in Food Science and Food Safety* vol. (9):pp. 3-20.

Jang et al. "Measurement of chlorine dioxide penetration in dairy process pipe biofilms during disinfection" 2006 *Applied Microbiology and Biotechnology* vol. (72):pp. 368-376.

Kaczur et al. "Chlorine oxygen acids and salts, chlorous acid, chlorites, and chlorine dioxide" 2000 *Kirk-Othmer Encyclopedia of Chemical Technology*.

Karpel et al. "Photodecomposition of chlorine dioxide and chlorite by u. v.-irradiation—Part II. Kinetic study" 1992 *Water Research* vol. (26):pp. 1665-1672.

Lee et al. "Efficacy of chlorine dioxide gas as a sanitizer of lettuce leaves" 2004 *Journal of Food Protection®* vol. (67):pp. 1371-1376.

Ruiz, R.P. "Karl Fischer Titration" 2001 *Current Protocols in Food Analytical Chemistry*, pp. A1.2.1-A1.2.4.

Scholz, E. Chapter 3 "Titration Techniques," *Karl Fischer titration: determination of water* 1984 *Springer-Verlag*, pp. 15-25.

Sy et al. "Evaluation of gaseous chlorine dioxide as a sanitizer for killing Salmonella, *Escherichia coli* O157:H7, Listeria monocytogenes, and yeasts and molds on fresh and fresh-cut produce" 2005 *Journal of Food Protection®* vol. (68):pp. 1176-1187.

Vogt et al. "Chlorine Oxides and Chlorine Oxygen Acids" 2005 *Ullmann's Encyclopedia of Industrial Chemistry.* Wiley-VCH Verlag GmbH & Co.KGaA.

Volk et al. "Implementation of chlorine dioxide disinfection: Effects of the treatment change on drinking water quality in a full-scale distribution system" 2002 *Journal of Environmental Engineering and Science* vol. (1):pp. 323-330.

Weaver-Meyers at al. "Controlling mold on library materials with chlorine dioxide: an eight-year case study" 1998 *The Journal of academic librarianship* vol. (24):pp. 455-458.

Whitney et al. "Inactivation of 'Bacillus anthracis spores" 2003 *Emerging infectious diseases* vol. (9):p. 623-627.

Wilson et al. "Effect of chlorine dioxide gas on fungi and mycotoxins associated with sick building syndrome" 2005 *Applied and Environmental Microbiology* vol. (71):pp. 5399-5403.

PCT Patent Application No. PCT/US2016/047603, filed Aug. 18, 2016; International Search Report / Written Opinion dated Nov. 3, 2016; 11 pages.

PCT Patent Application No. PCT/US2016/047608, filed Aug. 18, 2016; International Search Report / Written Opinion dated Nov. 15, 2016; 12 pages.

PCT Patent Application No. PCT/US2016/047612, filed Aug. 18, 2016; International Search Report / Written Opinion dated Nov. 11, 2016; 17 pages.

U.S. Appl. No. 15/753,312, filed Aug. 18, 2016, Abbott et al.

U.S. Appl. No. 15/753,314, filed Aug. 18, 2016, Abbott et al.

International Patent Application No. PCT/US2016/047603, filed Aug. 18, 2016; International Preliminary Report on Patentability dated Mar. 1, 2018; 7 pages.

International Patent Application No. PCT/US2016/047608, filed Aug. 18, 2016; International Preliminary Report on Patentability dated Mar. 1, 2018; 8 pages.

International Patent Application No. PCT/US2016/047612, filed Aug. 18, 2016; International Preliminary Report on Patentability dated Mar. 1, 2018; 8 pages.

Dehydration, Hawley's Condensed Chemical Dictionary, R.J. Lewis ed., Mar. 15, 2007 (Year: 2007).

\* cited by examiner

RELEASE OF ClO$_2$ GAS FROM MEDICAL DEVICE PACKAGING FILM

CROSS-REFERENCE TO RELATED APPLICATIONS

This application is a continuation of PCT Patent Application, PCT/US16/47608, filed on Aug. 18, 2016.which claims the benefit of U.S. Provisional Patent Application No. 62/206,464, filed on Aug. 18, 2015, which application is hereby incorporated herein by reference to the extent that it does not conflict with the present disclosure.

FIELD

This disclosure relates generally to the release of a disinfectant gas from packaging film for medical devices. In particular, the disclosure is directed to compositions and methods for the controlled release of ClO$_2$ gas from packaging for medical devices.

BACKGROUND

Chlorine dioxide (ClO$_2$) is a powerful oxidizing agent and disinfectant. It is used today primarily in bleaching processes in the paper pulp industry and as a disinfectant for water treatment. It has also been shown to be useful as a broad spectrum biocide in various applications such as food processing, fungus and mold fumigation, biofilm treatment and even in the killing of bedbugs and hardy anthrax spores.

Accordingly, it may be desirable to generate packaging films capable of releasing gaseous ClO$_2$ to inhibit microbial growth on products, such as medical devices, packaged in the films. However, timing and amount of release of ClO$_2$ gas from packaging films can be difficult to control.

Wellinghoff et al. have devised polymer packaging films which release ClO$_2$ gas when the films come in contact with moisture. See, for example, U.S. Pat. Nos. 5,360,609 and 5,888,528. In systems described in U.S. Pat. No. 5,360,609, a mixture of an acid anhydride and chlorite in different phases (hydrophobic and hydrophilic) can produce ClO$_2$ when the anhydride is hydrolyzed to produce an acid, which reacts with chlorite. Notably, this system produces ClO$_2$ upon contact with moisture from any source, and thus the timing of ClO$_2$ production can be difficult to control.

Wellinghoff et al. have also devised a polymeric composition containing chlorite anion and a photo-activated catalyst that triggers the production of ClO$_2$ upon exposure to light. See, for example, U.S. Patent Publication No. 2008/0299066. However, the timing of ClO$_2$ production in this system is difficult to control because ClO$_2$ is produced whenever the polymer is exposed to light, including inadvertent exposure to ambient visible light.

It would be desirable to provide a packaging for medical devices that allows for more controlled release of ClO$_2$ gas.

SUMMARY

Described herein, among other things, is a multilayer packaging film for medical devices that provides for controlled, on-demand release of ClO$_2$ gas to disinfect or sterilize a medical device packaged in the film. The packaging described herein releases ClO$_2$ gas upon exposure to both ultraviolet (UV) light and moisture.

In various embodiments, a multilayer package film is described herein. The multilayer medical device packaging film comprises a first layer and a chlorine dioxide-producing layer. The chlorine dioxide-producing layer comprises a polymer composition and a plurality of chlorite ions and is substantially free of an energy-activated catalyst and is substantially-free of an acid-releasing compound. Yet, the films described herein release chlorine dioxide when exposed to UV light in the presence of moisture.

The packaging described herein provides for more controlled release of ClO$_2$ gas than previously described chlorine dioxide-releasing films, such as those described by Wellinghoff et al. In addition, by requiring the use of UV light, rather than visible light-activated photocatalysts, such as those described by Wellinghoff et al., the medical device packaging films described herein do not release significant amounts of chlorine dioxide when exposed to ambient visible light. Accordingly, the films described herein can be manufactured and stored under typical lighting conditions, as opposed to in the dark, as well as manufactured and stored in humid conditions, without premature generation of chlorine dioxide. As such, the ability of the films described herein to release significant or effective amounts of chlorine dioxide at a desired time can be enhanced relative to previously described chlorine-generating compositions that include one or both of an acid-releasing compound and an energy-activated catalyst, which may be prematurely depleted of chlorite ions.

Additional features and advantages of the subject matter of the present disclosure will be set forth in the detailed description which follows, and in part will be readily apparent to those skilled in the art from that description or recognized by practicing the subject matter of the present disclosure as described herein, including the detailed description which follows, the claims, as well as the appended drawings.

It is to be understood that both the foregoing general description and the following detailed description present embodiments of the subject matter of the present disclosure, and are intended to provide an overview or framework for understanding the nature and character of the subject matter of the present disclosure as it is claimed. The accompanying drawings are included to provide a further understanding of the subject matter of the present disclosure, and are incorporated into and constitute a part of this specification. The drawings illustrate various embodiments of the subject matter of the present disclosure and together with the description serve to explain the principles and operations of the subject matter of the present disclosure. Additionally, the drawings and descriptions are meant to be merely illustrative, and are not intended to limit the scope of the claims in any manner.

BRIEF DESCRIPTION OF THE DRAWINGS

The following detailed description of specific embodiments of the present disclosure can be best understood when read in conjunction with the following drawings, where like structure is indicated with like reference numerals and in which.

Figure 1:
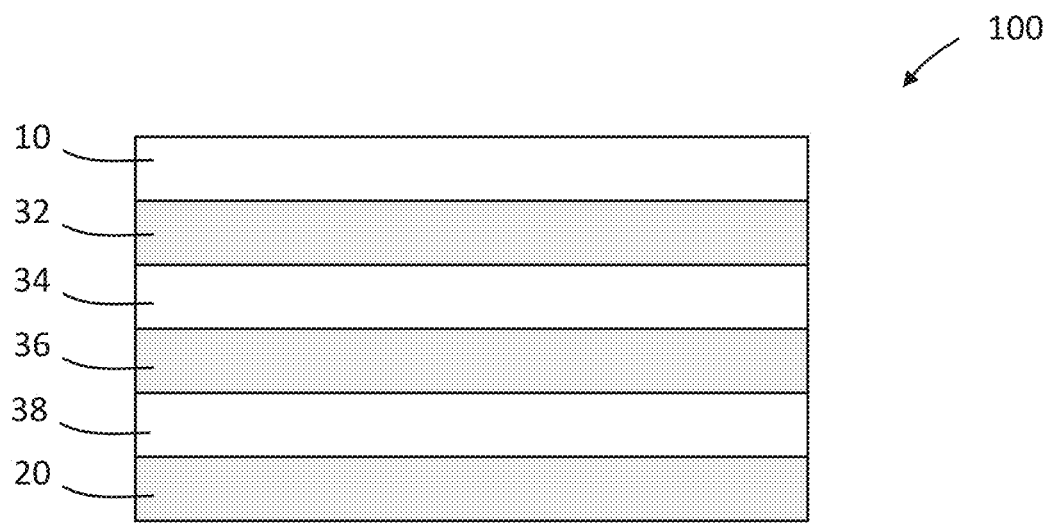
FIGS. 1-2 are schematic sectional views of embodiments of a multilayer packaging films.

The schematic drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar to other numbered components.

DETAILED DESCRIPTION

Reference will now be made in greater detail to various embodiments of the subject matter of the present disclosure, some embodiments of which are illustrated in the accompanying drawings.

The present disclosure describes packaging for medical devices that provides for controlled, on-demand release of $ClO_2$ gas to disinfect or sterilize a medical device packaged in the film. The packaging films described herein releases $ClO_2$ gas upon exposure to both UV light and moisture. Sufficient moisture may be present in the film due to manufacturing processes employed or environmental conditions in which the film is stored, such that the film or a package formed from the film may need only to be exposed to UV light to generate chlorine dioxide under conditions of a manufacturing line on which a medical device is packaged. Alternatively or in addition, the film may be exposed to an additional source of moisture for generation of chlorine dioxide following or during exposure to UV light.

The packaging is a multilayer packaging film comprising a first layer and a chlorine dioxide-producing layer. The chlorine dioxide-producing layer comprises a polymer composition and a plurality of chlorite ions. The chlorine dioxide-producing layer is substantially free of an energy-activated catalyst and is substantially free of an acid-releasing compound.

As used herein, an "energy-activated catalyst" is a compound that can catalyze the oxidation of $ClO_2^-$ to $ClO_2$ gas following activation of the catalyst compound by electromagnetic energy, such as visible light. Published U.S. Patent Application 2008/0299066A1 lists a number of compounds and classes of compounds as energy activated catalysts, some of which may be capable of catalyzing the oxidation of $ClO_2^-$ to $ClO_2$ gas following activation of the catalyst compound by electromagnetic energy. Published U.S. Patent Application 2008/0299066A1 lists metal oxides, metal sulfides, metal chalcogenites, metal phosphides, metal arsenides, non-metal semiconductors, photoactive homopolyanions, photoactive heteropolyanions, and polymeric semiconductors as examples of energy activated catalysts. The chlorine dioxide-producing layers of the films described herein are substantially free of those compounds that can catalyze the oxidation of $ClO_2^-$ to $ClO_2$ gas following activation of the catalyst compound by electromagnetic energy, particularly visible light.

Published U.S. Patent Application 2008/0299066A1 discloses examples in which titanium dioxide is used as an energy activated catalyst to catalyze the oxidation of $ClO_2^-$ to $ClO_2$ gas. In some embodiments, the chlorine dioxide-producing layers or the films described herein are substantially free of a metal oxide energy-activated catalyst. In some embodiments, the chlorine dioxide-producing layers or the films described herein are substantially free of titanium dioxide.

As used herein, an "acid-releasing compound" is a compound that, in the presence of moisture, can generate acid and hydronium ions, which hydronium ions can react with chlorite ions to form $ClO_2$ gas. U.S. Pat. No. 6,605,304 lists a number of acid releasing compounds for gas generation including carboxylic acids, esters, anhydrides, acyl halides, phosphoric acid, phosphate esters, trialkylsilyl phosphate esters, dialkyl phosphates, sulfonic acid, sulfonic acid esters, sulfonic acid chlorides, phosphosilicates, phosphosilicic anhydrides, carboxylates of poly a-hydroxy alcohols such as sorbitan monostearate or sorbitol monostearate, phosphosiloxanes, and acid releasing waxes, such as propylene glycol monostearate acid releasing waxes. U.S. Pat. No. 6,605,304 also lists as acid-releasing compounds inorganic acid releasing agents, such as polyphosphates, including tetraalkyl ammonium polyphosphates, monobasic potassium phosphate, potassium polymetaphosphate, sodium metaphosphates, borophosphates, aluminophosphates, silicophosphates, sodium polyphosphates such as sodium tripolyphosphate, potassium tripolyphosphate, sodium-potassium phosphate, and salts containing hydrolyzable metal cations such as zinc. In some embodiments described herein, the chlorine dioxide-producing layers or the films for generating $ClO_2$ gas described herein are substantially-free of such compounds.

In some embodiments, the chlorine dioxide-producing layers or the films described herein are substantially free of an anhydride. In some such embodiments, the chlorine dioxide-producing layer is substantially free of an alcohol, an amide, or an alcohol and an amide.

As used herein, "substantially free of an acid-releasing compound" means that the chlorine dioxide-producing layer includes no acid-releasing compound or includes 2% by weight or less of an acid-releasing compound. In some embodiments, the chlorine dioxide-producing layer includes no acid-releasing compound or includes 1% by weight or less, or 0.5% by weight or less, of an acid-releasing compound. In some embodiments, the ratio (by weight) of acid-releasing compound to chlorite ion source, such as chlorite ion salt, in the chlorine dioxide-producing layer is 1:10 or less. For example, the ratio of acid releasing compound to chlorite ion source may be 1:20 or less, such as 1:50 or less or 1:100 or less.

As used herein, "substantially free of an energy-activated catalyst" means that the chlorine dioxide-producing layer includes no energy-activated catalyst or includes less than 10 weight percent of an energy-activated catalyst based on the total weight of the layer. In some embodiments, the chlorine dioxide-producing layer includes less than 5 weight percent, such as less than 2 weight percent, of an energy-activated catalyst based on the total weight of the layer. In some embodiments, the ratio (by weight) of energy-activated catalyst to chlorite ion source, such as chlorite ion salt, in the chlorine dioxide-producing layer is 1:2 or less. For example, the ratio of energy-activated catalyst to chlorite ion source may be 1:5 or less, such as 1:10 or less or 1:20 or less.

One or more layers of the film, other than the chloride dioxide-producing layer(s), may include greater amounts of one or both of an energy-activated catalyst and an acid-releasing compound than the chloride dioxide-producing layer. One or more of layers of the film, other than the chlorine dioxide-producing layer(s), may also be substantially free of one or both of an energy-activated catalyst and an acid-releasing compound.

Preferably, the multilayer medical device packaging films described herein release an amount of chlorine dioxide for a sufficient amount of time to disinfect or sterilize a medical device packaged within the film when the film. Preferably, the film releases an amount of chlorine dioxide for a sufficient amount of time to sterilize a medical device packaged within the film.

As used herein, "disinfect" means to reduce the number of living bacteria. To determine whether a product is disinfected, a product that has undergone a disinfecting treatment, such as exposure to $ClO_2$ gas, can be compared to a control product that has not undergone the disinfecting treatment to determine whether bacterial burden has been reduced; and, if so, the product will be considered to have been disinfected. Alternatively, the bacterial burden of a product may be compared before and after treatment to determine whether the product has been disinfected. A medical device packaging film described herein may release any suitable amount of $ClO_2$ gas to disinfect a medical device disposed within packaging formed from the packaging film. For example, a film may release 10 parts per million (ppm) or greater $ClO_2$ gas into an interior volume defined by a package formed, at least in part, from the film. Typically, the film may release 50 ppm or greater $ClO_2$ gas to disinfect the medical device. The concentration of chlorine dioxide may increase over time if the package is sealed, as additional chlorine dioxide is released from the film. The amount of $ClO_2$ gas needed to effectively disinfect a medical device will depend, in part, on the nature of the device. In addition, the time that the medical device is exposed to $ClO_2$ gas will affect the ability of the $ClO_2$ gas to disinfect the medical device. In some embodiments, the film releases an amount of $ClO_2$ gas for a time sufficient to expose the medical device to 100 ppm.hours or greater of $ClO_2$ gas to disinfect the product. For example, the film may release 150 ppm.hours or more of $ClO_2$ gas, or 200 ppm.hours or more of $ClO_2$ gas, to disinfect the medical device.

As used herein, "sterilize" means to make free from bacteria or other living organisms. A multilayer medical device packaging film described herein may release any suitable amount of $ClO_2$ gas to sterilize a medical device disposed within a package formed by the film. For example, the film may release 200 parts per million (ppm) or greater $ClO_2$ gas into an interior volume defined by a package formed, at least in part, from the film. Typically, a composition may release 500 ppm or greater $ClO_2$ gas to sterilize the medical device. The amount of $ClO_2$ gas needed to effectively sterilize a medical device will depend, in part, on the nature of the device. In addition, the time that the medical device is exposed to $ClO_2$ gas will affect the ability of the $ClO_2$ gas to sterilize the device. In some embodiments, the film releases an amount of $ClO_2$ gas for a time sufficient to expose the medical device to 1000 ppm.hours or greater of $ClO_2$ gas to sterilize the device. For example, the film may release 1500 ppm.hours or more of $ClO_2$ gas, or 2000 ppm.hours or more of $ClO_2$ gas, to sterilize the medical device.

Packaging Film

The multilayer medical device packaging film comprises a first layer and a chlorine dioxide-producing layer. The first layer may be an oxygen barrier layer.

In many embodiments, the inner-most layer of the packaging film is the chlorine dioxide-producing layer. In some embodiments, the chlorine dioxide-producing layer is proximate to the inner-most layer of the film and the inner-most layer of the film allows transmission of chlorine dioxide through the inner-most layer. Upon exposure of the chlorine dioxide-producing layer to UV radiation and moisture, $ClO_2$ gas can be released to contact a medical device in a package produced by the packaging film. The amount of chlorite ion present in the packaging, the time and amount of exposure of the packaging to UV light and the time and amount of moisture to which the packaging is exposed can affect the amount of $ClO_2$ gas generated, and thus can affect the extent to which a medical is disinfected or whether the medical device is sterilized.

The packaging film may comprise any suitable number of layers. For example, the packaging film may comprise one or more of a sealing layer, a barrier layer, an abuse-resistant outer layer, an intermediate layer, a tie layer, and the like. The film may comprise one or more chlorine dioxide-producing layers.

Chlorine Dioxide-Producing Layer

The chlorine dioxide-producing layer comprises a plurality of chlorite ions and a polymer composition. The chlorite ions may be present in the layer in the form of a salt. The layer may include any suitable chlorite salt. Chlorite salts include both a chlorite anion and a cation. The cation can be an inorganic cation or an organic cation. For example, the cation may be any cation known in the art to be capable of forming a chlorite salt, including, without limitation, an alkali metal ion, and alkaline earth ion, a transition metal ion, a protonated primary amine, a protonated secondary amine, a protonated tertiary amine, a quaternary amine, or mixtures thereof. In some embodiments, the chlorite salt is selected from sodium chlorite and potassium chlorite. The chlorine dioxide-producing layer may include one or more chlorite salts. For example, the chlorine dioxide-producing layer may include sodium chlorite and potassium chlorite.

The chlorine dioxide-producing layer may include any suitable amount of chlorite salt. The amount of chlorite salt can be varied to help control the amount of $ClO_2$ that is generated. In non-limiting examples, the weight percent of the chlorite salt is, for example, 0.1%, 1%, 5%, 10%, 15%, 20%, 25%, 30%, 35%, 40%, 45%, 50%, 55%, 60%, 65% or 70% of the weight of the composition, or any amount in between. In some embodiments, the lower range of the weight of the chlorite salt may be, for example, 0.1%, 1%, 5%, 10%, 15%, 20%, 25%, 30%, 35%, 40%, 45%, 50%, 55%, 60%, or 65% of the weight of the composition, while the upper range of the weight of the chlorite salt may be 15%, 20%, 25%, 30%, 35%, 40%, 45%, 50%, 55%, 60%, 65%, or 70% of the weight of the composition. The disclosure encompasses all weight percentage ranges that are defined by any combination of these lower and upper bounds.

The chlorine dioxide-producing layer may comprise any suitable polymer composition. In some embodiments, the layer comprises one or more of polyethylene, ethylene vinyl acetate, ethylene alpha-olefins, or polypropylene.

The chlorine dioxide-producing layer may be present in any suitable form. For example, the layer may be in the form of a coating layer or a film layer. If the chlorine dioxide-producing layer is in the form of a film layer, the film layer may be co-extruded, laminated or otherwise associated with one or more other layer of the film.

The chlorine dioxide-producing layer may have any suitable thickness. In some embodiments, the layer has a thickness of 25 micrometers or more when the chlorine dioxide-producing layer is in the form of a film layer. A chlorine dioxide-producing film layer may have any suitable amount of chlorite ion in the layer, such as those amounts discussed above. In some embodiments, the chlorine dioxide-producing film layer comprises a chlorite salt in an amount within a range from 0.1 weight percent to 25 weight percent relative to the total weight of the layer. For example, the chlorine dioxide-producing film layer may comprise a chlorite salt in an amount within a range from 5 weight percent to 20 weight percent relative to the total weight of the layer.

In some embodiments, a coating comprising chlorite ions is disposed on a substrate layer to form the chlorine dioxide-producing layer on the substrate layer. The coating may be disposed across an entire surface of the substrate layer or can be disposed across one or more portions of the substrate layer. The coating comprising chlorite ions may be advantageously applied to certain portions of the substrate layer to direct the generation of $ClO_2$ gas only to areas where generation of $ClO_2$ gas is desired. Such directed coating and gas generation, can provide cost savings relative to coatings applied across an entire surface, including across areas for which gas generation is not needed or desired.

Any suitable coating composition may be used to coat the substrate layer. For example, the coating composition may comprise one or more chlorite salt, one or more other suitable coating components, and one or more suitable solvents or diluents. In some embodiments, the one or more coating components are water soluble or water dispersible.

Suitable coating components may include materials that retain the chlorite ions on the substrate layer after the article is coated on the substrate layer. In some embodiments, the coating composition comprises a polymer or resin compatible with the substrate layer to be coated. Upon drying or curing of the coating, the coating preferably adheres to the substrate layer.

The coating composition may comprise any suitable polymer. In some embodiments, the coating composition comprises one or more of polyethylene, ethylene vinyl acetate, ethylene alpha-olefins, or polypropylene.

The coating compositions may include any suitable amount of chlorite ion, such as the amounts discussed above. In some embodiments, the chlorite ions are present in a salt, and the salt is present in an amount within a range from 0.1 weight percent to 30 weight percent relative to the total weight of the chlorine dioxide-producing layer. For example, the salt may present in an amount within a range from 10 weight percent to 20 weight percent relative to the total weight of the chlorine dioxide-producing layer The coating composition may be applied in any suitable manner. For example, the substrate layer to be coated may be dipped in the coating composition or the coating composition may be sprayed, rolled, printed, or otherwise deposited on a surface of the substrate layer. In some embodiments, the coating is pattern coated to coat certain portions of a surface of the substrate layer and to leave certain portions of the substrate layer uncoated.

Heat Sealing Layers

The films described herein may comprise a heat sealing layer. The terms "heat seal layer" and "sealing layer" are used interchangeably and refer to a layer capable of fusion bonding by conventional indirect heating means which generate sufficient heat on at least one film contact surface for conduction to the contiguous film contact surface and formation of a bond interface therebetween without loss of the film integrity. The bond interface between contiguous inner layers preferably has sufficient physical strength to withstand the packaging process and subsequent handling.

In some embodiments, the heat seal layer comprises a polyolefin. "Polyolefin" is used herein broadly to include polymers such as polyethylene, ethylene-alpha olefin copolymers (EAO), polypropylene, polybutene, ethylene copolymers having a majority amount by weight of ethylene polymerized with a lesser amount of a comonomer such as vinyl acetate, and other polymeric resins falling in the "olefin" family classification. Polyolefins may be made by a variety of processes well known in the art including batch and continuous processes using single, staged or sequential reactors, slurry, solution and fluidized bed processes and one or more catalysts including for example, heterogeneous and homogeneous systems and Ziegler, Phillips, metallocene, single site and constrained geometry catalysts to produce polymers having different combinations of properties. Such polymers may be highly branched or substantially linear and the branching, dispersity and average molecular weight and may vary depending upon the parameters and processes chosen for their manufacture in accordance with the teachings of the polymer arts.

In some embodiments, the heat seal layer comprises a cyclic olefin copolymer (COC), such as an ethylene norbornene copolymer.

In some embodiments, the heat seal layer comprises one or more of polyethylene, ethylene vinyl acetate, ethylene alpha-olefins, or polypropylene.

In some embodiments, the sealing layer comprises a blend of polymers to obtain suitable or desired properties.

In various embodiments, the sealing layer can facilitate formation of hermetically sealed packages when heat sealed.

In some embodiments, the sealing layer is the chlorine dioxide-producing layer that is capable of generating $ClO_2$ gas upon exposing the film to UV light and moisture. The sealing layer can form the inner-most layer of a package and can thus advantageously place the chlorite ions for generating $ClO_2$ gas in close proximity to an article packaged in the film or to be packaged in the film. The sealing layer may comprise any suitable amount of chlorite ion. However, increasing amounts of chlorite ion, for example in the form of chlorite salt, may interfere with the ability of the layer to seal. Typically, the heat seal layer will comprise less than about 70% by weight chlorite salt, such as 50% or less, 30% or less, 20% or less, or 10% or less. In some embodiments, the heat seal layer comprises a chlorite salt in an amount within a range from 0.1 weight percent to 25 weight percent relative to the total weight of the layer. For example, the heat seal layer comprises a chlorite salt in an amount within a range from 5 weight percent to 20 weight percent relative to the total weight of the layer.

A sealing layer may have any suitable thickness. In some embodiments, a sealing layer has a thickness of 25 micrometers or greater.

If chlorite ions are dispersed in a sealing layer or another layer, the polymer or polymers forming the layer are preferably transparent to UV radiation (e.g., at least 50% of UV light can be transmitted through the polymers forming the sealing layer). However, if the polymer is not particularly transparent to UV light, the intensity of the UV radiation to which the layer is exposed can be increased to expose the chlorite ions to sufficient UV radiation. In addition or alternatively, the thickness of the layer may be decreased to enhance the percentage of the thickness of the layer thorough which sufficient radiation penetrates and/or the concentration of the chlorite ions in the layer can be increased.

In some embodiments, a coating comprising chlorite ions is disposed on the heat seal layer to form the chlorine dioxide-producing layer on the heat seal layer. The coating may be disposed across an entire inner surface of the sealing layer or can be disposed across one or more portions of the sealing layer. For example, the coating may be applied to a portion of the sealing layer that is not involved in heat sealing. Accordingly, the presence of the chlorite ions, for example in the form of chlorite salts, will not adversely affect the heat sealability of the heat seal layer.

Barrier Layers

A packaging film as described herein may include one or more barrier layer. If included, a barrier layer preferably functions both as a gas barrier layer, and as a moisture barrier layer, although these functions may be provided by separate layers. A gas barrier layer is preferably an oxygen barrier layer, and is preferably a core layer positioned between and protected by surface layers. For example, an oxygen barrier layer can be in contact with a first surface layer and an adhesive layer or may be sandwiched between two tie layers, two surface layers, or a tie layer and a surface layer.

A gas barrier, such as a chlorine dioxide barrier or an oxygen barrier, is preferably selected to provide sufficiently diminished permeability of gases to protect a medical device disposed in the sealed packaging from undesirable deterioration or, for example, oxidative processes. For example, a film may comprise an oxygen barrier having an oxygen permeability that is low enough to prevent oxidation of medical devices to be packaged in the film. In some embodiments, a multilayer packaging film will have an oxygen transmission rate ($O_2TR$) of less than 150 $cm^3/m^2$/24 hours at 1 atmosphere and 23° C., such as less than 10 $cm^3/m^2$ per 24 hours at 1 atmosphere. To protect oxygen sensitive articles from deterioration from oxygen contact over time, the films may have an $O_2TR$ of less than 1, such as less than 0.1, less than 0.01, or less than 0.001 $cm^3/m^2$ per 24 hours at 1 atmosphere and 23° C.

A moisture barrier is preferably selected to provide a moisture permeability sufficiently diminished to protect an article disposed in the sealed packaging from undesirable deterioration. For example, a film may comprise a water barrier having a moisture permeability that is low enough to prevent deleterious effects upon packaged articles such as medical devices. A preferred film according to various embodiments will have a water vapor transmission rate (WVTR) of less than 15 $g/m^2$ per 24 hours at 38° C. and 90% RH. In some embodiments, a film has a WVTR of less than 1, less than 0.1, or less than 0.01 $g/m^2$ per 24 hours at 38° C. and 90% RH.

A barrier layer can comprise any suitable material and may be any suitable thickness. A gas barrier layer can comprise polyvinyl alcohol (PVOH), ethylene vinyl alcohol (EVOH), polyvinylidene chloride (PVDC), polyamide, polyester, polyalkylene carbonate, polyacrylonitrile, a nanocomposite, a metallized film such as aluminum vapor deposited on a polyolefin, etc., as known to those of skill in the art. Suitable moisture barrier layers include aluminum foil, PVDC, fluoropolymers like polychlorotrifluoroethylene (PCTFE), polyolefins such as HDPE, LLDPE and cyclic olefin copolymers (COC), and metallized films such as aluminum vapor deposited on a polyolefin, etc., as known to those of skill in the art.. It is desirable that the thicknesses of the barrier layers are selected to provide the desired combination of the performance properties sought e.g. with respect to oxygen permeability, water vapor permeability, delamination resistance, etc.

A bulk layer may be provided to provide additional functionality such as stiffness or heat sealability or to improve machinability, cost, flexibility, barrier properties, etc. Preferred bulk layers comprise one or more polyolefins such as polyethylene, ethylene-alpha olefin copolymers (EAO), polypropylene, polybutene, ethylene copolymers having a majority amount by weight of ethylene polymerized with a lesser amount of a comonomer such as vinyl acetate, and other polymeric resins falling in the "olefin" family classification. The bulk layer may be of any suitable thickness or may even be omitted for use in certain applications.

If a film comprises a moisture barrier, care may need to be taken to ensure that the chlorine dioxide producing layer (e.g., a chlorite ion-containing sealing layer or coating layer) of the film is capable of being exposed to sufficient moisture to release $ClO_2$ gas. In some embodiments, the atmosphere of the packaging manufacturing line can be controlled to ensure that the chlorite-containing layer is exposed to sufficient moisture. In some embodiments, the packaging may be in the form of a three-sided bag with the article (e.g., food product, pharmaceutical product, medical device, or other product) disposed in the bag prior to final sealing of the fourth side to seal the product in the bag. While the product is in the three-sided bag, moist gas such as a stream of nitrogen containing steam or heated water may be used to flush the bag and to provide sufficient moisture for generation of $ClO_2$ gas prior to final sealing. In some embodiments, the packaging films may be stored in a high moisture environment prior to being brought on-line for packaging.

Abuse-Resistant Outer Layer

The films described herein may include an outer layer. Since it is seen by the user/consumer, in both monolayer and multilayer embodiments, the exterior surface of the film preferably has desirable optical properties and may have high gloss. Also, it preferably withstands contact with sharp objects and provides abrasion resistance, and for these reasons it is often termed the abuse resistant layer. This exterior abuse-resistant layer may or may not also be used as a heat sealable layer and thus may comprise one or more suitable heat seal polymers such as polyethylene or polypropylene. As the exterior surface layer of the film, this layer most often is also the exterior layer of any package, bag, pouch or other container made from the film, and is therefore subject to handling and abuse e.g. from equipment during packaging, and from rubbing against other packages and shipping containers and storage shelves during transport and storage.

The exterior surface layer should be easy to machine (i.e. be easy to feed through and be manipulated by machines e.g. for conveying, packaging, printing or as part of the film or bag manufacturing process). Suitable stiffness, flexibility, flex crack resistance, modulus, tensile strength, coefficient of friction, printability, and optical properties are also frequently designed into exterior layers by suitable choice of materials. This layer may also be chosen to have characteristics suitable for creating desired heat seals which may be resistance to burn through e.g. by impulse sealers or may be used as a heat sealing surface in certain package embodiments e.g. using overlap seals.

Suitable exterior surface layers may comprise: paper, oriented polyester, amorphous polyester, polyamide, polyolefin, cast or oriented nylon, polypropylene, or copolymers, or blends thereof. Oriented films of this or any other layer may be either uni-axially or bi-axially oriented. The exterior layer thickness is typically 0.5 to 2.0 mils. Thinner layers may be less effective for abuse resistance, however thicker layers, though more expensive, may advantageously be used to produce films having unique highly desirable puncture resistance and/or abuse resistance properties.

In some embodiments, the abuse layer is transparent to UV light.

Intermediate Layers

A packaging film described herein may include an intermediate layer. An intermediate layer is any layer between the exterior layer and the interior layer and may include oxygen barrier layers, tie layers or layers having functional attributes useful for the film structure or its intended uses. Intermediate layers may be used to improve, impart or otherwise modify a multitude of characteristics: e.g. printability for trap printed structures, machinability, tensile properties, flexibility, stiffness, modulus, designed delamination, easy opening features, tear properties, strength, elongation, optical, moisture barrier, oxygen or other gas barrier, radiation selection or barrier e.g. to ultraviolet wavelengths, etc. Suitable intermediate layers may include: adhesives, adhesive polymers, paper, oriented polyester, amorphous polyester, polyamide, polyolefin, nylon, polypropylene, or copolymers, or blends thereof. Suitable polyolefins may include: polyethylene, ethylene-alpha olefin copolymers (EAO), polypropylene, polybutene, ethylene copolymers having a majority amount by weight of ethylene polymerized with a lesser amount of a comonomer such as vinyl acetate, and other polymeric resins falling in the "olefin" family classification, LDPE, HDPE, LLDPE, EAO, ionomer, ethylene methacrylic acif (EMA), ethylene acrylic acid (EAA), modified polyolefins e.g. anhydride grafted ethylene polymers, etc.

Tie Layers

A film as described herein may comprise one or more adhesive layers, also known in the art as "tie layers," which can be selected to promote the adherence of adjacent layers to one another in a multilayer film and prevent undesirable delamination. A multifunctional layer is preferably formulated to aid in the adherence of one layer to another layer without the need of using separate adhesives by virtue of the compatibility of the materials in that layer to the first and second layers. In some embodiments, adhesive layers comprise materials found in both the first and second layers. The adhesive layer may suitably be less than 10% and preferably between 2% and 10% of the overall thickness of the multilayer film.

Multilayer films can comprise any suitable number of tie or adhesive layers of any suitable composition. Various adhesive layers are formulated and positioned to provide a desired level of adhesive between specific layers of the film according to the composition of the layers contacted by the tie layers.

The interior, exterior, intermediate or tie layers may be formed of any suitable thermoplastic materials, for example, polyamides, polystyrenes, styrenic copolymers e.g. styrene-butadiene copolymer, polyolefins, and in particular members of the polyethylene family such as LLDPE, VLDPE, HDPE, LDPE, COC, ethylene vinyl ester copolymer or ethylene alkyl acrylate copolymer, polypropylenes, ethylene-propylene copolymers, ionomers, polybutylenes, alpha-olefin polymers, polyesters, polyurethanes, polyacrylamides, anhydride-modified polymers, acrylate-modified polymers, polylactic acid polymers, or various blends of two or more of these materials.

Optional Additives to Layers

Various additives may be included in the polymers utilized in one or more of the exterior, interior and intermediate or tie layers of packaging comprising the same. For example, a layer may be coated with an anti-block powder. Also, conventional anti-oxidants, antiblock additives, polymeric plasticizers, acid, moisture or gas (such as oxygen) scavengers, slip agents, colorants, dyes, pigments, organoleptic agents may be added to one or more film layers of the film or it may be free from such added ingredients Reflective Layers The packaging films may include one of more layers that reflect UV light. Examples of suitable materials for such layers include metallic oils or depositions like vacuum metallized or sputtered layers. The reflective layer could be applied as a coating where reflective particles such as metallic flakes are dispersed in a polymeric binder. The film may be configured such that the chlorine dioxide-producing layer is positioned between the reflective layer and the UV source when the film is exposed to UV radiation. In some such embodiments, the one or more reflective layer(s) is/are in contact with the polymeric film. The reflective layers may be optically engineered to maximize yield, by increasing UV exposure of the chlorite salts dispersed within the film (e.g., dispersed within a sealing layer or a coating disposed on the sealing layer).

In cases where the polymers or additives of one or more layers of the film are not transparent to UV light (e.g., block transmission of more than 50% of UV light) or reflect UV light, care may need to be taken to ensure that the chlorine dioxide-producing layer (e.g., seal layer or coating disposed on seal layer) can be exposed to sufficient amounts of UV radiation to generate $ClO_2$ gas. In some embodiments, a packaging film is subjected to UV radiation prior to final sealing of the packaging to ensure that the chlorine dioxide-producing layer is subjected to sufficient UV radiation to generate $ClO_2$ gas. For example, the packaging manufacturing line can be equipped with an appropriate UV emitting source to allow in-line UV irradiation of the chlorine dioxide-producing layer.

Methods of Manufacture

The packaging films described herein may be made in any suitable manner, such as by conventional processes. Processes to produce flexible films may include e.g. cast or blown film processes, or extruding processes.

Packages may be formed from films in any suitable manner. In some embodiments, the packages are formed by heat sealing a film to itself or another suitable film. In some embodiments, packages such as pouches are thermoformed. In some embodiments, films are heat sealed across an opening of a container.

Film Thickness

A packaging film described herein may have any suitable thickness. In some embodiments, the packaging film has a total thickness of less than about 50 mils, more preferably the film has a total thickness of from about 1.0 to 10 mils (25-250 microns (µ), such as from about 1 to 5 mils, or from about 2 to 3.5 mils. For example, entire multilayer films or any single layer of a multilayer film can have any suitable thicknesses, including 1, 2, 3, 4, 5, 6, 7, 8, 9, 10 or 50 mils, or any increment of 0.1 or 0.01 mil therebetween.

In some embodiments, the packaging films are as thick as 50 mils (1270 microns) or higher, or as thin as 1 mil (25.4 microns) or less. In various embodiments, the packaging films have a thickness of between about 2-4 mil (51-102 microns).

Tearing Aid or Tear Initiator

The packaged articles that include an article disposed within sealed packaging may include a tearing aid or tear initiator such as a notch. Examples of tearing aids or tear initiators include notches, slits, perforations, surface roughened portions, etc. Such tear initiators may be used on one or more edges of a package such as a pouch.

Advantageously the tear initiator may be used with scoring e.g. mechanical or laser scoring of one or more layers, preferably the other abuse resistance layer, to create a tear directing line which facilitates opening.

Examples of Embodiments of Multilayer Films

In some embodiments, a multilayer medical packaging film comprises a first layer, and a chlorine dioxide-producing layer. The chlorine dioxide-producing layer comprises a polymer composition and a plurality of chlorite ions. The chlorine dioxide-producing layer is substantially free of an energy-activated catalyst and is substantially free of an acid-releasing compound. In some embodiments, the plurality of chlorite ions are present in a salt selected from the group consisting of sodium chlorite, potassium chlorite, and mixtures thereof. In some embodiments, the first layer is an oxygen barrier layer comprising aluminum foil, metal coated polymer, metal oxide coated polymer, or an aromatic polyamide polymer. In some embodiments, the first layer is an oxygen barrier layer comprising an ethylene vinyl alcohol copolymer, a polyvinylidene chloride copolymer, or an aliphatic polyamide. In some embodiments, the first layer is an outer layer proximate the chlorine dioxide-producing layer, wherein the outer layer comprises at least one of polyethylene or polypropylene. In some embodiments, the first layer is an abuse-resistant layer, wherein the abuse-resistant layer is UV-light transparent.

In some embodiments, the chlorine dioxide-producing layer is a coating having a thickness less than 15 µm. In some embodiments, the coating comprises at least one of polyethylene, ethylene vinyl acetate, ethylene alpha-olefins, or polypropylene. In some embodiments, the coating comprises a chlorite salt in an amount within a range from 0.1 weight percent to 30 weight percent relative to the total weight of the chlorine dioxide-producing layer. For example, the coating comprises a chlorite salt in an amount within a range from 10 weight percent to 20 weight percent relative to the total weight of the chlorine dioxide-producing layer.

In some embodiments, the chlorine dioxide-producing layer has a thickness of at least 25 µm. In such embodiments, the polymer composition may comprise at least one of polyethylene, ethylene vinyl acetate, ethylene alpha-olefins, or polypropylene. The plurality of chlorite ions may be present in a salt, and the salt may be present in an amount within a range from 0.1 weight percent to 25 weight percent relative to the total weight of the chlorine dioxide-producing layer, such as within a range from 5 weight percent to 20 weight percent relative to the total weight of the chlorine dioxide-producing layer.

In some embodiments, the medical package comprises a sidewall comprising the multilayer medical packaging film. The medical package comprises an interior volume defined by an inside surface of the sidewall. In some embodiments, the chlorine dioxide-producing layer is proximate the inside surface of the sidewall.

In some embodiments, the multilayer medical packaging film has a layer composition in the following sequence: (i) a layer of polyethylene; (ii) the chlorine dioxide-producing layer; (iii) a tie layer; (iv) the first layer comprising an oxygen barrier layer; (v) a tie layer; and (vi) an abuse layer. The film may also have optional additional layers dispersed within the sequence.

Referring now to FIG. 1, a multilayer medical packaging film 100 is shown. The film 100 includes a first layer 10, which may be an outer layer (as depicted) but can be an inner layer or a layer between the inner and outer layer. The film 100 also includes a chlorine dioxide-producing layer 20 that contains a polymer composition and chlorite ions. The chlorine dioxide-producing layer 20 can be a film layer or a coating layer. The depicted film 100 includes optional intervening layers 32, 34, 36, and 38.

Figure 2:
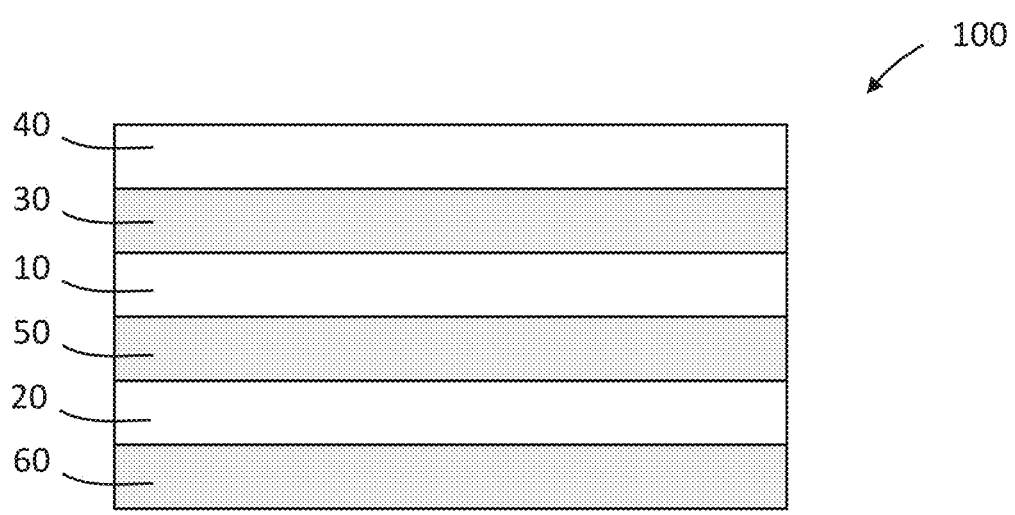

Referring now to FIG. 2, a multilayer medical packaging film 100 is shown. The film 100 includes in the following sequence: a layer 60 of polyethylene; the chlorine dioxide-producing layer 20; a tie layer 50; the first layer 10 comprising an oxygen barrier layer; a tie layer 30; and an abuse layer 40. The film 100 may comprise optional intervening layers (not shown).

Figure 3:
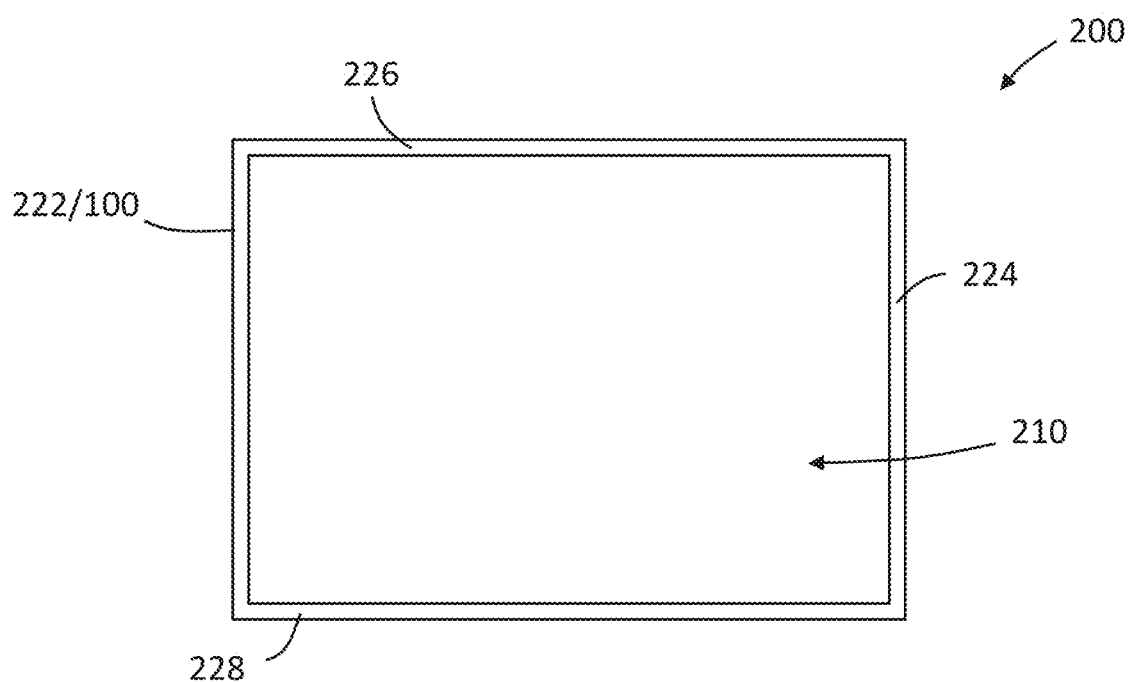
FIG. 3 is a schematic sectional view of an embodiment of a medical package.

Referring now to FIG. 3, a medical package 200 is shown. The depicted package 200 includes first 222, second 224, third 226, and fourth 228 sidewalls that at least partially define an interior volume 210 of the package. The first sidewall 222 comprises a multilayer packaging film 100 comprising a chlorine dioxide-producing layer. The other sidewalls 224, 226, 228 may or may not include a multilayer packaging film having a chlorine dioxide-producing layer.

Packaged Products

Any suitable medical device may be disposed in a package comprising the multilayer packaging film described herein. For example, catheters such as balloon dilatation catheters, guide catheters, aspiration catheters, and diagnostic catheters; vacutainers; yankauers; enteral feeding kits; dressing gowns and drapes; coronary stents; surgical tools and equipment; or the like may be disposed within a sealed package as described herein. Preferably, the packaging generates a sufficient amount of $ClO_2$ gas for a sufficient amount of time after being exposed to UV light and moisture to sterilize the medical device.

Gas Generation

The films, packages or packaged produce described herein may be exposed to UV radiation and moisture in any suitable manner to generate chlorine dioxide from the chlorine dioxide-producing layer(s). The films may be exposed first to moisture and then to UV light, first to UV light and then moisture, or simultaneously exposed to UV light and moisture to release $ClO_2$. Sufficient moisture may be present in the film or in a package formed from the film, for example due to the manufacturing process used to produce the film or the environmental conditions, such that the film or package need only be exposed to UV light to produce $ClO_2$.

In some embodiments, the films, packages or packaged produce are first exposed to UV light and then later exposed to moisture to generate chlorine dioxide. The films, packages or packaged medical devices that have previously been exposed to UV light may be exposed to any suitable source of moisture to generate chlorine dioxide. For example, the films, packages, or packaged produce may be exposed to water vapor or humidified gas.

The amount of $ClO_2$ generated from a film as described herein can be regulated by, for example, varying the wavelength and exposure time of the ultraviolet light, the amount of water vapor (moisture) present, the concentration of chlorite salts in the composition, or the length of the storage period.

In some embodiments, the UV light has a wavelength in the range of about 200 nm to 400 nm. In some such embodiments, the UV light has a wavelength in the range of about 230 nm to 320 nm. In some such embodiments, the UV light has a wavelength in the range of about 240 nm to 280 nm. Preferably, the UV light includes light having a wavelength of 254 nm.

In some embodiments, the packaged device, package or film is exposed to UV light for a period of time that is greater than 10 milliseconds. In some such embodiments, the packaged device, package or film is exposed to UV light for a period of time that is greater than 10 seconds. In some such embodiments, the packaged device, package or film is exposed to UV light for a period of time that is greater than ten minutes.

In some embodiments, the step of exposing the packaged device, package or film to ultraviolet light may be repeated one or more times, as can the step of subsequently contacting the packaged device, package or film with moisture to generate $ClO_2$ gas.

In some embodiments, packaged device, package or film is exposed to humidified gas. The humidified gas may have any suitable relative humidity. For example, the relative humidity of the humidified gas may be within the range of about 1% to 100%. In some such embodiments, the relative humidity of the humidified gas is within the range of about 20% to 100%. In some such embodiments, the relative humidity of the humidified gas is within the range of about 60% to 100%. In some such embodiments, the relative humidity of the humidified gas is within the range of about 75% to 100%.

In some embodiments, the steps of (a) exposing the packaged device, package or film including a chlorine dioxide-producing layer to UV light, and (b) subsequently contacting the packaged device, package or film with moisture, are separated by an intervening storage time. In some such embodiments, the intervening storage time is within the range of about one minute to about two days. In some such embodiments, the storage time is within the range of about one hour to about one day.

In some embodiments, the method further includes the step of drying the packaged device, package or film including a chlorine dioxide-producing layer before exposing the packaged device, package or film to UV light. In some such embodiments, the step of drying the packaged device or film is performed by contacting the packaged device, package or film with a dry gas or subjecting to a drying oven.

In some embodiments, the method further includes the step of heating the packaged device, package or film.

In some embodiments, a method for generating $ClO_2$ gas includes the steps of (a) exposing a packaged device, package or film including a chlorine dioxide-producing layer to ultraviolet (UV) light, and (b) subsequently exposing the packaged device, package or film to moisture, whereby $ClO_2$ gas is generated. Alternatively, the method includes the steps of (a) exposing a packaged device, package or film including a chlorine dioxide-producing layer to moisture, and (b) subsequently exposing the packaged device, package or film to ultraviolet (UV) light. Optionally, these steps may be repeated one or more times to generate additional amounts of $ClO_2$ gas.

As used herein and in the appended claims, the singular forms "a," "an," and "the" include plural reference unless the context clearly dictates otherwise. As well, the terms "a" (or "an"), "one or more" and "at least one" can be used interchangeably herein. The terms "comprising," "including," and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference for all purposes.

The following examples are offered for illustrative purposes only, and is not intended to limit the scope of the present invention in any way. Indeed, various modifications of the invention in addition to those shown and described herein will become apparent to those skilled in the art from the foregoing description and the following examples and fall within the scope of the appended claims.

EXAMPLES

Varying Amounts of Energy-Activated Catalyst

Equal parts of titanium dioxide (99.1% TiO2; Sigma-Aldrich, St. Louis, Mo.) and sodium chlorite (technical grade; 80% NaClO2; Sigma-Aldrich, St. Louis, Mo.) were mixed and suspended in water, and subsequently left in an open container until most of the water evaporated. The samples were evaporated (but not dried) in complete darkness, without exposure to visible or UV light sources. Similar blends were made with 2:1, 10:1, 20:1, and 65:1 sodium chlorite to titanium dioxide ratios. For testing, individual samples of the blends were placed in small glass vials of volume 20 mL and hermetically sealed. After sealing, the vials were exposed to a compact fluorescent light source for approximately 4.5 hours. A $ClO_2$ detector (PortaSens II, Analytical Technology Inc., Collegeville, Pa.) was used to measure the concentration of the gas generated (see results in Table 1). Subsequently, the samples were exposed to a UV light source (254 nm, Spectrolinker) for 15 seconds. Again, the concentration of $ClO_2$ in the vials was measured and is reported in Table 1.

TABLE 1

Concentration of $ClO_2$ after fluorescent light and UV light exposure.
The upper detection limit of the sensor was 240 ppm.

| Sample Reference | Sample mass (g) | $NaClO_2$ to $TiO_2$ to weight ratio | $ClO_2$ concentration after fluorescent light exposure | $ClO_2$ concentration after UV (254 nm) light exposure |
|---|---|---|---|---|
| Sample 1 | 2.31 | 1:1 | >240 ppm | >240 ppm |
| Sample 2 | 1.83 | 2:1 | >240 ppm | >240 ppm |
| Sample 3 | 1.55 | 10:1 | 171 ppm | >240 ppm |
| Sample 4 | 1.50 | 20:1 | 196 ppm | >240 ppm |
| Sample 5 | 1.46 | 65:1 | 151 ppm | >240 ppm |
| Sample 6 | 1.39 | $NaClO_2$ only | 63 ppm | >240 ppm |

Self Sterilizing Pouch Example 1

A 35 weight percent aqueous sodium chlorite (technical grade; 80% $NaClO_2$; Sigma-Aldrich, St. Louis, Mo.) solution was prepared and compounded into resin pellets of ExxonMobil EXACT® 3040 (ethylene-hexene copolymer; density=0.900 g/cm3; melt index=17 dg/min; ExxonMobil Chemical Company, Baytown, Tex.) using a 50 mm co-rotating twin screw extruder. The resulting resin had a sodium chlorite content of 7.4% by weight.

The sodium chlorite-containing resin was cast into a film via melt extrusion process using a 3 layer flat die extrusion system. Layers of EVOH and LDPE were extruded simultaneously with the sodium chlorite-containing resin in a co-extrusion process to produce a 25 cm wide, three-layer sheet such that the layers were arranged as follows: 1.5 mil LDPE/1.5 mil EVOH/1 mil LLDPE sodium chlorite. Monolayer films of EVA (DuPont Elvax® 3124 EVA) were also produced. These contained no sodium chlorite.

Self-sterilizing pouches were made from the film by heat-sealing the two edges of film specimens (30 cm length, 15 cm width) folded onto themselves with the sodium chlorite-containing resin layer on the inside. Self-Contained Biological indicators (SCBI) (NAMSA, Northwood, Ohio) containing $1.3 \times 10^6$ bacterial spores (*Bacillus atrophaeus*) were inserted in the pouches and heat-sealed, completing a hermetic package. Some pouches contained 0.2 ml of water to provide additional moisture. Some SCBIs were covered with aluminum foil to protect them from UV light. Some of the pouches were conditioned in a low RH environment to remove the residual moisture from the film. Using ASTM Method D6869-03(2011) Standard Test Method for Coulometric and Volumetric Determination of Moisture in Plastics Using the Karl Fischer Reaction (the Reaction of Iodine with Water), the films were found to have moisture levels of more than 4,000 ppm prior to removing residual moisture and less than 500 ppm after removing residual moisture. The variables with and without foil verify that the UV light itself is not affecting the bacterial spores in the SCBI. The pouches containing SCBIs were exposed to a total of 675 J/cm2 of UV radiation (λ: 254 nm) by exposing each pouch for 180s (90s-each side) to UV light inside a Spectrolinker XL-1500 (contains six Phillips G15T8 low-pressure mercury lamps; 0.66 W/cm/bulb; Spectronics Corporation, Westbury, N.Y.). The pouches were incubated in a laminar hood overnight. The SCBIs were taken out and 'activated' by pushing in their lids, thereby breaking the growth media-containing ampule inside. They were incubated at 35° C. and evaluated after 48 hours for color change from green to yellow. A color change to yellow indicates a change in pH caused by the growth of surviving bacterial spores. A color of green indicates that no bacterial spores survived. Table 2 summarizes the samples that were tested and the results.

TABLE 2

Different samples tested in experiments to determine sterilizing efficacy of self-sterilizing pouches

| Pouch Spec. | Foil covering on SCBI | Residual Moisture Present? | Additional moisture in pouch (in ml) | Exposure to UV (254 nm) | Resulting SCBI color |
|---|---|---|---|---|---|
| LDPE/EVOH/ LLDPE-NaClO2 | No | Yes | 0 | None | Yellow |
| LDPE/EVOH/ LLDPE-NaClO2 | No | Yes | 0.2 | None | Yellow |
| EVA3124 monolayer | Yes | Yes | 0 | 180 sec. | Yellow |
| EVA3124 monolayer | No | Yes | 0 | 180 sec. | Yellow |
| LDPE/EVOH/ LLDPE-NaClO2 | No | Yes | 0.2 | 180 sec. | Green |
| LDPE/EVOH/ LLDPE-NaClO2 | No | Yes | 0 | 180 sec. | Green |
| LDPE/EVOH/ LLDPE-NaClO2 | Yes | Yes | 0.2 | 180 sec. | Green |
| LDPE/EVOH/ LLDPE-NaClO2 | Yes | Yes | 0 | 180 sec. | Green |
| LDPE/EVOH/ LLDPE-NaClO2 | No | No | 0 | 180 sec. | Yellow |

Self Sterilizing Pouch Example 2

A sodium chlorite containing resin and film was produced using the same procedure as described in Self Sterilizing Pouch Example 1. The resulting film had a structure of 1.5 mil LDPE/1.5 mil EVOH/1.5 mil sodium chlorite (16% by weight) containing LLDPE.

Self-sterilizing pouches were made from the film by heat-sealing the two edges of film specimens (30 cm length, 15 cm width) folded onto themselves with the sodium chlorite-containing resin layer on the inside. These pouches were placed in a high humidity environment (35C, 80% RH) for approximately 12 hours. Self-Contained Biological indicators (SCBI) were inserted in a pouch of interest along with vacutainers (small devices made of rigid plastics, used to draw a fixed amount of blood from a patient) and heat-sealed, completing a hermetic package. The pouches were exposed to 254 nm UV for 180 seconds. When the pouches were cut open, the $ClO_2$ gas alert detector was used to see if any $ClO_2$ remained in the packages.

SCBIs in pouches containing vacutainers (3 replicates) were sterilized, as indicated by a green color after breaking the ampule and incubating, after exposure to UV and moisture. Also, residual $ClO_2$ was measured to be approximately 0.14 ppm in all pouches (with or without vacutainers) when they were opened after 24 hours.

All publications and patents specifically mentioned herein are incorporated by reference for all purposes. Those skilled in the art will recognize, or be able to ascertain using no more than routine experimentation, numerous equivalents to the specific materials and methods described herein. Such equivalents are considered to be within the scope of this invention and encompassed by the following claims.

We claim:

1. A multilayer medical packaging film comprising:
   a first layer, and
   a chlorine dioxide-producing layer comprising a polymer composition and a source of a plurality of chlorite ions;
   wherein the chlorine dioxide-producing layer comprises less than 2% by weight of an energy-activated catalyst and comprises no acid-releasing compound, wherein the weight ratio of the energy-activated catalyst to the source of the plurality of chlorite ions is 1:20 or less, and
   wherein the chlorine dioxide-producing layer produces a sufficient amount of chlorine dioxide when exposed to UV light and moisture to disinfect or sterilize a medical device packaged in the film.

2. The multilayer medical packaging film according to claim 1, wherein the source of the plurality of chlorite ions comprises a salt selected from the group consisting of sodium chlorite, potassium chlorite, and mixtures thereof.

3. The multilayer medical packaging film according to claim 1, wherein the first layer is an oxygen barrier layer; wherein the oxygen barrier layer comprises aluminum foil, metal coated polymer, metal oxide coated polymer, or an aromatic polyamide polymer.

4. The multilayer medical packaging film according to claim 1, wherein the first layer is an oxygen barrier layer; wherein the oxygen barrier layer comprises ethylene vinyl alcohol copolymer, polyvinylidene chloride copolymer, or an aliphatic polyamide.

5. The multilayer medical packaging film according to claim 1, wherein the chlorine-dioxide-producing layer is a coating having a thickness less than 15 μm.

6. The multilayer medical packaging film according to claim 5, wherein the polymer composition comprises at least one of polyethylene, ethylene vinyl acetate, ethylene alpha-olefins, or polypropylene.

7. The multilayer medical packaging film according to claim 5, wherein the source of the plurality of chlorite ions comprises a salt, and the salt is present in an amount within a range from 0.1 weight percent to 30 weight percent relative to the total weight of the chlorine dioxide-producing layer.

8. The multilayer medical packaging film according to claim 5, wherein the source of the plurality of chlorite ions comprises a salt, and the salt is present in an amount within a range from 10 weight percent to 20 weight percent relative to the total weight of the chlorine dioxide-producing layer.

9. The multilayer medical packaging film according to claim 1, wherein the chlorine dioxide-producing layer has a thickness of at least 25 μm.

10. The multilayer medical packaging film according to claim 9, wherein the polymer composition comprises at least one of polyethylene, ethylene vinyl acetate, ethylene alpha-olefins, or polypropylene.

11. The multilayer medical packaging film according to claim 9, wherein the source of the plurality of chlorite ions comprises a salt, wherein the salt is present in an amount within a range from 0.1 weight percent to 25 weight percent relative to the total weight of the chlorine dioxide-producing layer.

12. The multilayer medical packaging film according to claim 9, wherein the source of the plurality of chlorite ions comprises a salt, wherein the salt is present in an amount within a range from 5 weight percent to 20 weight percent relative to the total weight of the chlorine dioxide-producing layer.

13. The multilayer medical packaging film according to claim 1, wherein the first layer is an outer layer proximate the chlorine dioxide-producing layer, wherein the outer layer comprises at least one of polyethylene or polypropylene.

14. The multilayer medical packaging film according to claim 1, wherein the first layer is an abuse-resistant layer, wherein the abuse-resistant layer is UV-light transparent.

15. The multilayer medical packaging film according to claim 1, wherein the film has a layer composition in the following sequence:
  a layer of polyethylene;
  the chlorine dioxide-producing layer;
  a tie layer;
  the first layer comprising an oxygen barrier layer;
  a tie layer; and
  an abuse layer,
wherein optional additional layers may be dispersed within said sequence.

16. A medical package comprising a sidewall comprising the multilayer medical packaging film according to claim 1, wherein the medical package comprises an interior volume defined by an inside surface of the sidewall.

17. The medical package according to claim 16, wherein the chlorine dioxide-producing layer is proximate the inside surface of the sidewall.

18. The medical package according to claim 16, wherein the chlorine dioxide-producing layer has a surface area smaller than the inside surface of the sidewall.

19. The multilayer medical packaging film of claim 1, wherein the chlorine dioxide-producing layer comprises no energy-activated catalyst.

* * * * *